(12) United States Patent
Xue

(10) Patent No.: US 9,427,302 B2
(45) Date of Patent: Aug. 30, 2016

(54) STENT HAVING A C-SHAPED BODY SECTION FOR USE IN A BIFURCATION

(75) Inventor: Yueqiang Xue, Dublin (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 1164 days.

(21) Appl. No.: 12/421,381

(22) Filed: Apr. 9, 2009

(65) Prior Publication Data

US 2010/0262216 A1 Oct. 14, 2010

(51) Int. Cl.
*A61F 2/06* (2013.01)
*A61F 2/07* (2013.01)
*A61F 2/856* (2013.01)

(52) U.S. Cl.
CPC . *A61F 2/06* (2013.01); *A61F 2/07* (2013.01); *A61F 2/856* (2013.01); *A61F 2002/065* (2013.01); *A61F 2002/067* (2013.01); *A61F 2230/0013* (2013.01); *A61F 2230/0069* (2013.01)

(58) Field of Classification Search
CPC ............... A61F 2002/064; A61F 2002/05; A61F 2/954; A61F 2002/821; A61F 2230/006; A61F 2/856; A61F 2230/00696
USPC ............ 623/1.11, 1.15, 1.16, 1.35, 1.2
See application file for complete search history.

(56) References Cited

U.S. PATENT DOCUMENTS

| | | | |
|---|---|---|---|
| 3,757,031 A * | 9/1973 | Izraeli | H02G 15/113 138/155 |
| 5,458,639 A | 10/1995 | Tsukashima et al. | |
| 5,507,769 A | 4/1996 | Marin et al. | |
| 5,755,734 A * | 5/1998 | Richter et al. | 606/194 |
| 6,129,756 A * | 10/2000 | Kugler et al. | 623/1.27 |
| 6,231,597 B1 * | 5/2001 | Deem | A61B 17/12022 606/108 |
| 6,251,133 B1 | 6/2001 | Richter et al. | |
| 6,471,719 B1 | 10/2002 | Voinov et al. | |
| 6,500,147 B2 | 12/2002 | Omaleki et al. | |
| 6,524,336 B1 | 2/2003 | Papazolgou et al. | |
| 6,554,795 B2 | 4/2003 | Bagaoisan et al. | |
| 6,652,571 B1 * | 11/2003 | White | A61F 2/90 623/1.13 |
| 6,730,119 B1 | 5/2004 | Smalling | |
| 6,736,827 B1 | 5/2004 | McAndrew et al. | |
| 6,802,858 B2 | 10/2004 | Gambale et al. | |
| 7,264,632 B2 | 9/2007 | Wright et al. | |
| 8,951,298 B2 * | 2/2015 | Shalev | A61F 2/07 623/1.11 |
| 2004/0111148 A1 * | 6/2004 | Goodson | A61F 2/07 623/1.16 |
| 2006/0161244 A1 * | 7/2006 | Seguin | A61F 2/07 623/1.23 |
| 2006/0235459 A1 * | 10/2006 | Das | A61F 2/954 606/192 |
| 2007/0061002 A1 * | 3/2007 | Paul | A61F 2/2418 623/1.13 |
| 2007/0156229 A1 | 7/2007 | Park | |
| 2007/0219612 A1 * | 9/2007 | Andreas et al. | 623/1.11 |
| 2008/0195190 A1 * | 8/2008 | Bland | A61F 2/91 623/1.11 |
| 2010/0036477 A1 * | 2/2010 | Bronson | A61F 2/856 623/1.15 |
| 2010/0070019 A1 * | 3/2010 | Shalev | A61F 2/06 623/1.15 |
| 2011/0264184 A1 * | 10/2011 | Heltai | A61F 2/06 623/1.1 |
| 2016/0000589 A1 * | 1/2016 | Xue | A61F 2/07 623/1.35 |

* cited by examiner

*Primary Examiner* — Christian Sevilla
*Assistant Examiner* — Seema Mathew

(57) ABSTRACT

A bifurcation stent system includes a pair of self-expanding stents. Each stent has a C-shaped body section having a generally semicircular cross-section along its length and an O-shaped body section having a circular cross-section along its length. The stents are deployed in vivo such that the edges of the C-shaped body sections abut each other to form a tubular scaffold in a Y-shaped formation that conforms to the bifurcation. In order to connect the stents in vivo, the C-shaped body sections are configured to include a ball and socket connection there between. The C-shaped body sections align and abut to form a tubular scaffold that extends in the main vessel of the bifurcation, while the O-shaped body sections are tubular scaffolds that extend into the respective branch legs of the bifurcation.

11 Claims, 6 Drawing Sheets

STENT HAVING A C-SHAPED BODY SECTION FOR USE IN A BIFURCATION

FIELD OF THE INVENTION

The invention relates generally endoluminal prostheses, and more particularly to a stent system intended for placement in a bifurcated vessel of a patient.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes.

Various types of endoluminal prostheses are also known, each providing a component for modifying the mechanics of the targeted luminal wall. For example, stent prostheses are known for implantation within body lumens for providing artificial radial support to the wall tissue, which forms the various lumens within the body, and often more specifically within the blood vessels of the body.

To provide radial support to a blood vessel, such as one that has been widened by percutaneous transluminal coronary angioplasty, commonly referred to as "angioplasty," "PTA" or "PTCA", a stentlis implanted in conjunction with the procedure. Under this procedure, the stent may be collapsed to an insertion diameter and inserted into a body lumen at a site remote from the diseased vessel. The stent may then be delivered to the desired treatment site within the affected lumen and deployed, by self-expansion or mechanical dilation, to its desired diameter for treatment.

Although systems and techniques exist that work well in many cases, no technique is applicable to every case. For example, special methods exist for dilating lesions that occur in branched or bifurcated vessels. A bifurcation is an area of the vasculature where a main vessel is bifurcated into two or more branch vessels. It is not uncommon for stenotic lesions to form at such bifurcations. The stenotic lesions can affect only one of the vessels, i.e., either of the branch vessels or the main vessel, two of the vessels, or all three vessels.

Implanting a stent at a bifurcation in a body lumen poses various challenges for the effective treatment of stenoses in the lumen. For example, dilating a vessel at a bifurcation may cause narrowing of an adjacent branch of the vessel. In response to such a challenge, attempts to simultaneously dilate both branches of the bifurcated vessel have been pursued. These attempts include deploying more than one balloon, more than one prosthesis, a bifurcated prosthesis, or some combination of the foregoing.

However, stent implantation at a bifurcation is particularly prone to undesirable reactions such as restenosis, inflammation, infection, thrombosis, and proliferation of cell growth that occludes the passageway because a bulk of material (such as, for example, overlapping or abutting stent struts) often occurs at some point along the bifurcation and acts as an initiation site for thrombus and/or restenosis. For example, when abutting stents are deployed in each of the branch or leg vessels, often abutting stent material extends across the middle of the main vessel thus interrupting the blood flow path. To assist in preventing these conditions, stents have been used with coatings to deliver drugs or other therapeutic agents at the site of the stent. However, it would be desirable to provide a bifurcation stent system having a design or structure that allows for less turbulent blood flow therethrough and thus minimizes undesirable reactions such as those listed above. Accordingly, there exists a need in the art to eliminate or decrease the amount of stent metal that is left in the blood flow path of the main vessel of the bifurcation.

BRIEF SUMMARY OF THE INVENTION

A stent system includes a first stent prosthesis and a second stent prosthesis. The first stent prosthesis has a first C-shaped body section and a first O-shaped body section, the first C-shaped body section having a generally C-shaped cross-section along its length and the first O-shaped body section having a generally O-shaped cross-section along its length. Similarly, the second stent prosthesis has a second C-shaped body section and a second O-shaped body section, the second C-shaped body section having a generally C-shaped cross-section along its length and the second O-shaped body section having a generally O-shaped cross-section along its length. The first stent prosthesis and the second stent prosthesis are configured to be deployed and maintained in vivo such that edges of the first C-shaped body section and the second C-shaped body section abut each other to form a tubular scaffold.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
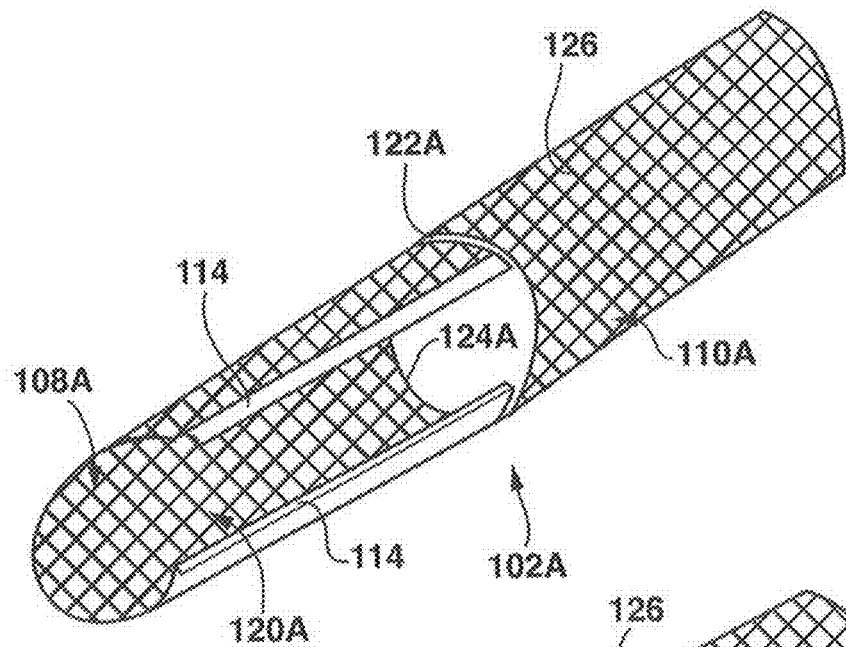
FIG. 1 is a schematic perspective view of a first stent prosthesis configured for placement at a bifurcation, according to an embodiment hereof.
Figure 2:
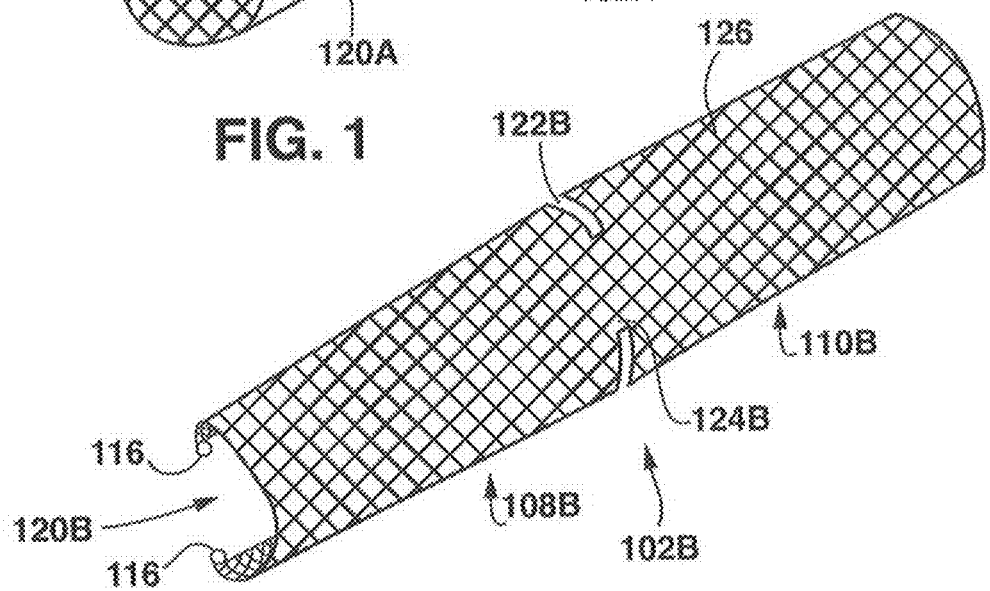
FIG. 2 is a schematic perspective view of a second stent prosthesis configured for placement at a bifurcation, according to an embodiment hereof.
Figure 3:
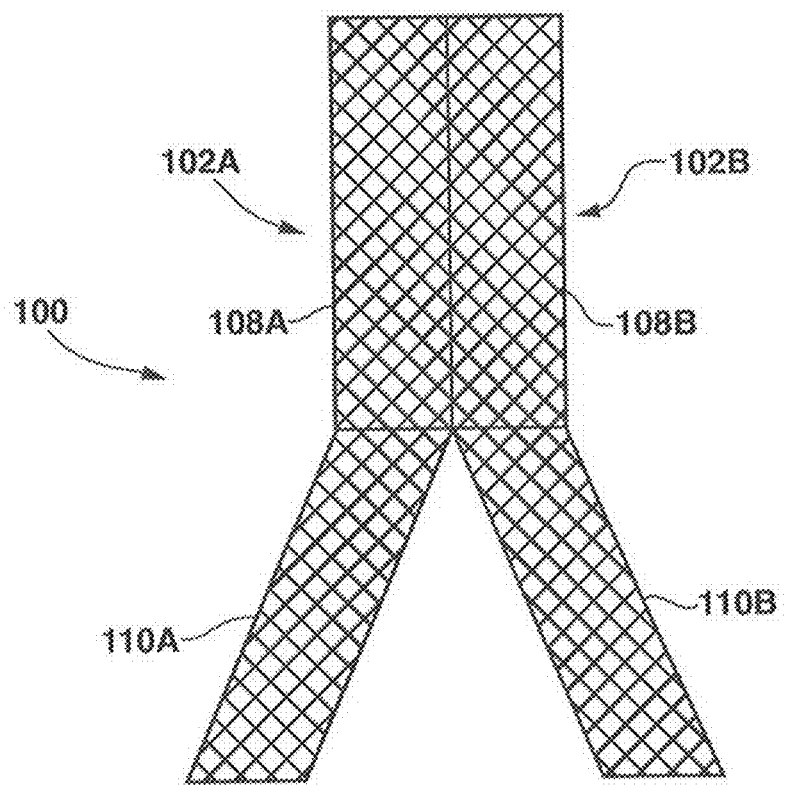
FIG. 3 is a side view of a stent system configured for placement at a bifurcation, the stent system including the first stent prosthesis of FIG. 1 and the second stent prosthesis of FIG. 2.
Figures 4, 5:
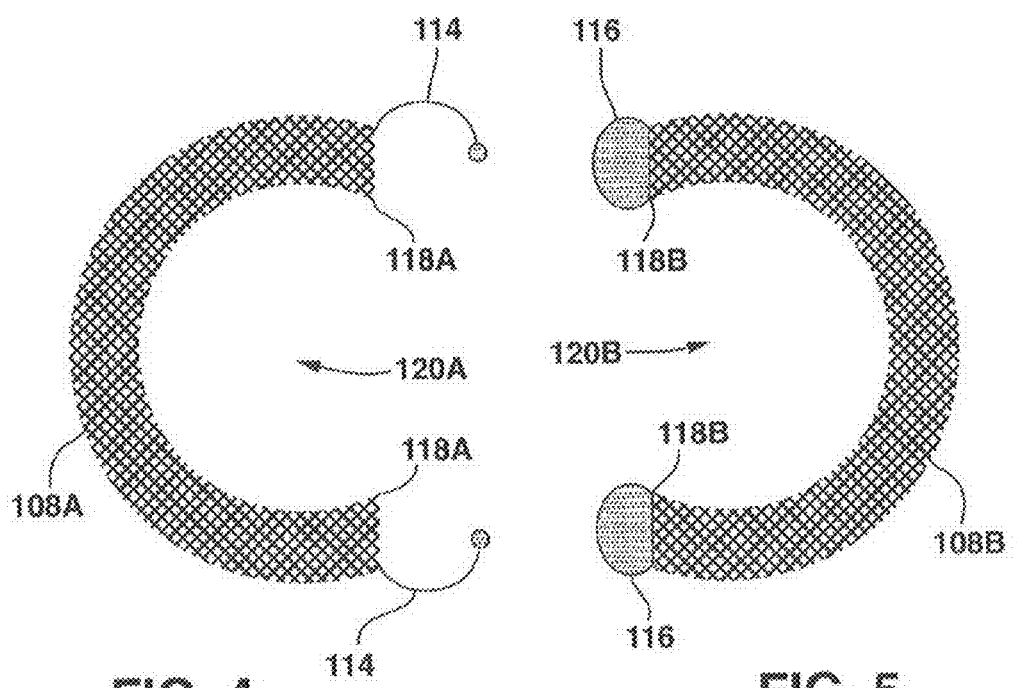
FIG. 4 is a schematic cross-sectional illustration of the C-shaped body section of the first stent prosthesis of FIG. 1.
FIG. 5 is a schematic cross-sectional illustration of the C-shaped body section of the second stent prosthesis of FIG. 2.

Referring to FIGS. 1-3, a stent system 100 configured for placement in a bifurcation includes a pair of abutting stents, a first stent 102A and a second stent 102B. As shown in FIG. 1, first stent 102A is a self-expanding prosthesis. First stent 102A has a hollow hemicylindrical or C-shaped body section 108A and a hollow cylindrical or O-shaped body section 110A. C-shaped body section 108A has a generally semicircular or C-shaped transverse cross-section along its length, and O-shaped body section 110A has a circular or ellipsoidal transverse cross-section along its length. C-shaped body section 108A includes an open portion 120A. As best shown in FIG. 4, the C-shaped cross-section comprises between 50% and 75% of the circumference of a circle. The lengths of C-shaped body section 108A and O-shaped body section 110A may vary according to the particular application. Similarly, as shown in FIG. 2, second stent 102*b* is a self-expanding prosthesis. Second stent 102B has a C-shaped body section 108B and an O-shaped body section 110B. C-shaped body section 108B has a generally semicircular or C-shaped transverse cross-section along its length including an open portion 120B, and O-shaped body section 110B has a circular or ellipsoidal transverse cross-section along its length. As best shown in FIG. 5, the C-shaped cross-section comprises between 50% and 75% of the circumference of a circle. The lengths of C-shaped body section 108B and O-shaped body section 110B may vary according to the particular application.

First stent 102A and second stent 102B are formed from struts or frame members 126. Frame members 126 may be formed into first stent 102A and second stent 102B using any of a number of different methods. For example, the stents may be formed by laser or chemical etching or another method of cutting frame members 126 out of a solid wall metal tubing. Alternatively, frame members 126 may be wires or filaments and may be braided around a mandrel and welded or otherwise mechanically coupled to form the stents. The stents may alternatively be manufactured in any other method that would be apparent to one skilled in the art.

O-shaped body sections 110A, 110B are coupled to C-shaped body sections 108A, 108B at junctions 124A, 124B, respectively. Junctions 124A, 124B may simply be an area where frame members 126 of O-shaped body sections 110A, 110B are continuous with frame members 126 of C-shaped body sections 108A, 108B. O-shaped body sections 110A, 110B and C-shaped body sections 108A, 108B may be coupled together by other means known to those skilled in the art, for example and not by way of limitation, welding, adhesive, or mechanical coupling. Gaps 122A, 122B are disposed between a portion of C-shaped body sections 108A, 108B and a portion of O-shaped body sections 110A, 110B, respectively. Gaps 122A, 122B permit the C-shaped body portions to expand to a different diameter than the O-shaped body portions.

As shown in FIG. 3, first stent 102A and second stent 102B are deployed in vivo side by side in, an abutting arrangement to form stent system 100. When deployed, stent system 100 has a Y-shaped formation with a trunk and two legs extending therefrom. The trunk and legs of the Y-shaped formation each have a tubular body with a generally circular or ellipsoidal cross-section. In the exemplary embodiments illustrated herein, the lengths of C-shaped body sections 108 and O-shaped body sections 110 are similar. As would be understood by one of ordinary skill in the relevant art, however, the relative lengths and diameters of the C-shaped and O-shaped body sections are variable and may be selected depending on the length and diameter of the vessel desired to be supported by stent system 100. Similarly, O-shaped body sections 110A and 110B may have different lengths and/or expanded diameters to fit the targeted branch vessels. However, C-shaped body sections 108A and 108B have substantially the same length such that once aligned and abutted; they form a tubular scaffold that is the trunk of the Y-shaped formation. O-shaped body sections 110A and 110B are tubular scaffolds that are the legs of the Y-shaped formation. Once implanted at a bifurcation, stent system 100 provides artificial radial support to the wall tissue with the trunk of the Y-shaped formation located within the main vessel of the bifurcation and the legs of the Y-shaped formation located in the branch legs of the bifurcation, respectively. Since the trunk tubular prosthesis is formed by C-shaped bodies 108A and 108B, there is no stent material disposed in the blood flow path of the main vessel of the bifurcation (best shown in FIG. 6), reducing the likelihood of thrombus, especially as compared to known bifurcation stents with abutting D-shaped sections that produce a double-layered web along the center line of the blood flow path.

In order to properly align and connect in vivo, C-shaped body sections 108A and 108B of first stent 102A and second stent 102B, respectively, may be configured to include a ball and socket connection there between. The ball and socket connection is a mechanical interlock having each male component of second stent 102B, received within a corresponding female component of the first stent 102A. More particularly, as shown in the cross-sectional view of FIG. 4, C-shaped body section 108A of first stent 102A includes one or more female sockets or receptacles 114 along the length thereof. In one embodiment, multiple sockets 114 are included along the length of C-shaped body section 108A and occur in facing pairs on opposing edges 118A of the C-shaped cross-section. In another embodiment, as shown in FIG. 1, an elongate groove or channel-shaped socket 114 may extend the entire length of edges 118A of stent 102A. As shown in the cross-sectional view of FIG. 5, C-shaped body section 108B of second stent 102B includes one or more male tabs or balls 116 along the length thereof. In one embodiment, multiple tabs 116 occur along the length of C-shaped body section 108B and occur in facing pairs on opposing edges 118B of the C-shaped cross-section. In another embodiment, an elongate male tab 116 may extend the entire length of edges 118B of stent 102B. Male tabs 116 are configured to fit within sockets 114 of first stent 102A.

Figure 6:
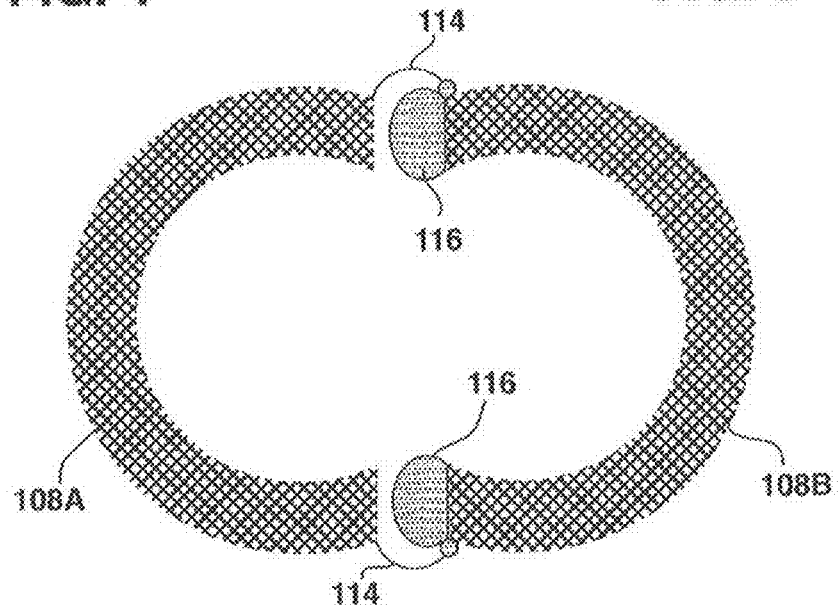
FIG. 6 is a schematic cross-sectional illustration of the stent system of FIG. 3, with the C-shaped body sections of first and second stent prostheses joined via a ball and socket connection therebetween.

FIG. 6 illustrates C-shaped body section 108A of first stent 102A and C-shaped body section 108B of second stent 102B joined together with male tabs 116 of second stent 102B received within-sockets 114 of first stent 102A. To assist in accurately positioning stent system 100 such that first stent 102A and second stent 102B are aligned side by side, female receptacles 114 and male tabs 116 may be formed of platinum, gold, silver, palladium, iridium, or any other metal that is generally visible in-vivo using X-ray fluoroscopy.

First stent 102A and second stent 102B are self-expanding. Self-expanding as used herein means that first stent 102A and second stent 102B each have a mechanical memory to return to an expanded or deployed configuration. Mechanical memory may be imparted to the stents by thermal treatment to achieve a spring temper in stainless steel, for example, or to set a shape memory in a susceptible metal alloy, such as nitinol. Thus, in embodiments here of first stent 102A and second stent 102B may be made from stainless steel, a pseudo-elastic metal such as nitinol, or a so-called super alloy, which may have a base metal of nickel, cobalt, chromium, or other metal. As will be explained in more detail below, a sheath is provided to surround and contain each stent 102A, 102B in a radially compressed, reduced size for delivery into a vessel. Once each stent is positioned within the vessel at the target site such as, for example within the bifurcation, the sheath may be retracted proximally, thus releasing each stent to radially expand by its own internal restoring forces and engage the occlusion as well as the wall of the vessel. Thus, each self-expanding stent can have two states of size or shape, a contracted or compressed configuration suitable for transluminal delivery to the treatment site and a deployed or expanded configuration for contacting the vessel wall.

Figure 8:
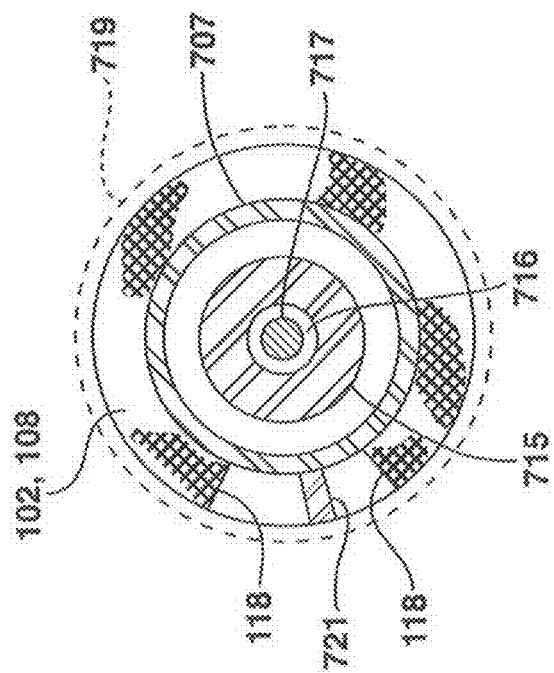
FIG. 8 is a cross-sectional view taken along line 8-8 of FIG. 7.
Figure 7:
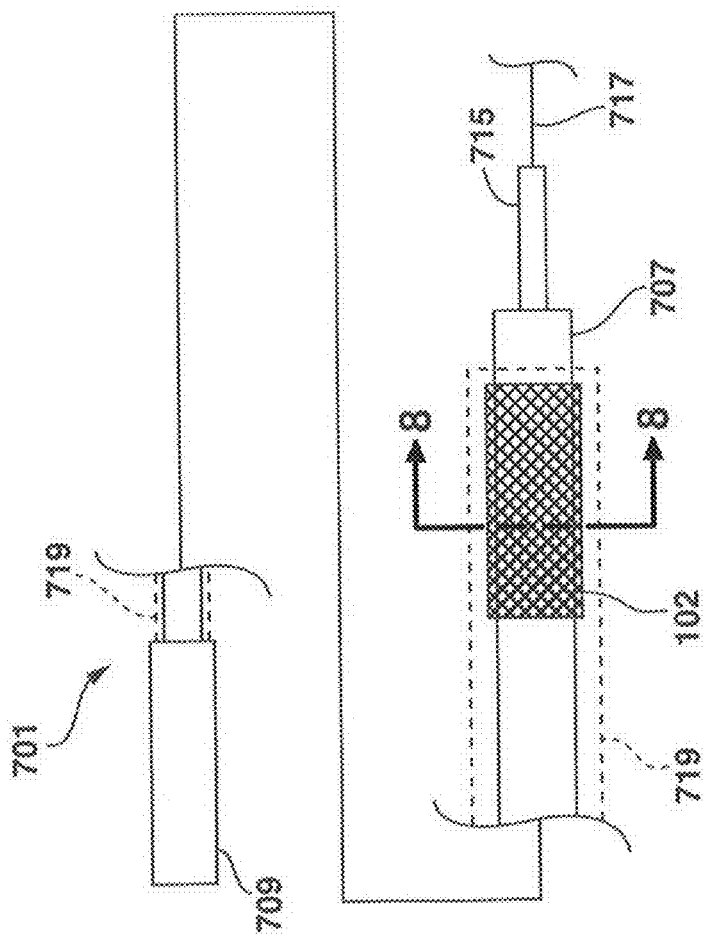
FIG. 7 is a side view schematic of an exemplary stent delivery system, according to an embodiment hereof.

FIG. 7 shows a schematic, side view of a stent delivery system 701 that may be used to delivery stents 102 to a target location. FIG. 8 shows a cross-sectional view of the delivery system 701 through C-shaped body section 108 of stent 102, the view taken along line 8-8 of FIG. 7. Delivery-system 701 may be a conventional self-expanding stent delivery system, such as the system described in U.S. Pat. No. 7,264,632 to Wright et al., which is hereby incorporated by reference in its entirety, or other such similar delivery systems that are well known in the art. Delivery system 701 includes a catheter shaft 707 and may include a guidewire shaft 715 disposed therethrough. A guidewire 717 may be disposed through guidewire lumen 716 of guidewire shaft 715. Catheter shaft 707 is coupled at its proximal end to a handle 709, which includes a guidewire port for access to the guidewire lumen 716. As described herein, guidewire shaft 715 extends the entire length of catheter shaft 707 in an over-the-wire configuration. However, as would be understood by one of ordinary skill in the art, in a rapid-exchange configuration, guidewire shaft 715 may alternatively extend only within the distal portion of catheter shaft 707 such that guidewire lumen 716 exits shaft 707 in a distal region.

Stent 102 is positioned over catheter shaft 707. Stent 102 may be mounted in delivery system 701 with either C-shaped body section 108 or O-shaped body-section 110 disposed closest to the distal end of the system, depending on whether the targeted vessel bifurcation is to be approached in antegrade or retrograde fashion with respect to blood flow therethrough. For example, a coronary artery bifurcation is typically approached in antegrade fashion with the catheter system entering the coronary ostium from the aorta. In this example, stent 102 is mounted such that O-shaped body section 110 is closest to the distal end of the delivery system 701 since the branch vessel to be supported by O-shaped body section 110 will be located distally of the main branch. In another example, an aortic bifurcation is typically approached in retrograde fashion with bilateral catheter entries in both femoral arteries. In this example, stent 102 is mounted such that C-shaped body section 108 is closest to the distal end of the delivery system 701 since the aorta to be supported by C-shaped body section 10 will be located distally of the femoral branch artery.

As best shown in FIG. 8, a sheath 719 (shown in phantom in FIG. 7) surrounds and contains stent 102 in a reduced size for delivery through the vasculature to target site. A pull mechanism (not shown) at handle 709 is coupled to sheath 719 such that sheath 719 may be pulled proximally to release stent 102 from sheath 719, as would be understood by one skilled in the art. Stent 102 may be compressed to cover, in transverse cross-section, approximately 75% to 99% of the circumference of shaft 707. Edges 118 of the C-shaped body section 108 of stent 102 preferably do not touch or overlap each other. In one embodiment, a stop 721 (shown in FIG. 8) may be provided between shaft 707 and sheath 719 to ensure that the edges 118 of the C-shaped body section 108 of stent 102 do not interfere with each other when stent 102 is compressed onto the shaft 707. Stop 721 may be coupled to shaft 707.

As explained in more detail below, after sheath 719 has been retracted to release self-expanding stent 102, a balloon may be utilized to further expand stent 102 or to properly align stents 102A and 102B. Such a balloon may be part of a separate balloon catheter inserted after delivery system 701 has been removed. Alternatively, the portion of shaft 707 upon which stent 102 is mounted may be expandable. In such an embodiment, after sheath 719 is retracted, an inflation fluid may be injected between shaft 707 and guidewire shaft 715 to expand the expandable portion of shaft 707 and further expand stent 102. Conventional balloon catheters such as those shown or described in U.S. Pat. Nos. 6,736,827; 6,554,795; 6,500,147; and 5,458,639, which are incorporated by reference herein in their entirety, may be used in such an alternative embodiment.

Figure 9:
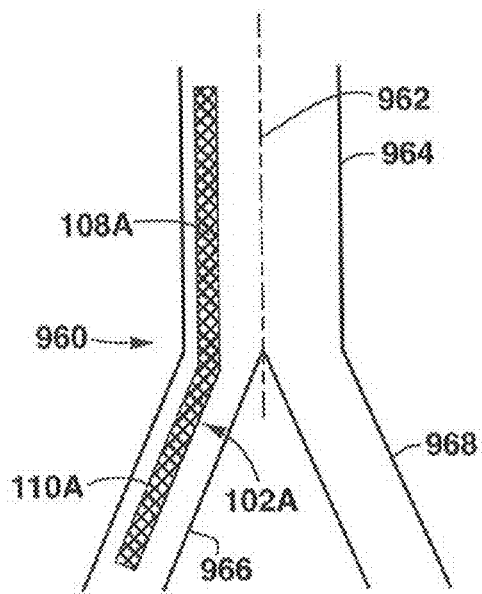
FIGS. 9-16 are schematic illustrations of a method of delivering and deploying the stent system of FIG. 3 at a bifurcation according to an embodiment hereof.

A method of delivering and deploying stent system 100 to a vessel bifurcation 960 according to an embodiment hereof is described with reference to FIGS. 9-16. As shown in FIG. 9, the bifurcated vessel 960 includes a main or trunk vessel 964, a first branch vessel 966, and a second branch vessel 968. Bifurcated vessel 960 may include target tissue, for example, a lesion (not shown) which may include plaque obstructing the flow of blood through bifurcated vessel 960. The lesion may be located along at least part of main vessel 964, first branch vessel 966, and/or second branch vessel 968. The stent delivery system is not shown in FIGS. 9-16 for convenience.

Figure 10:
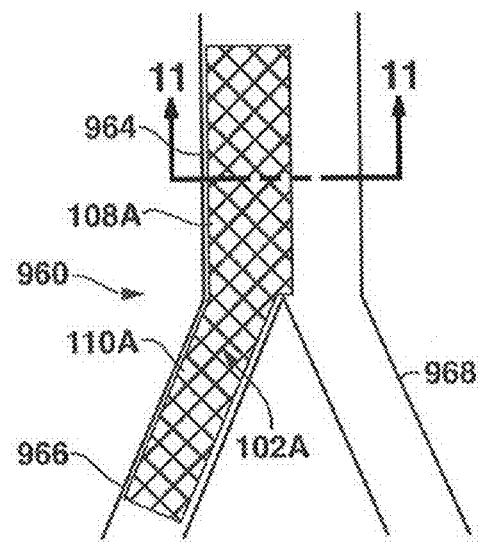
Figure 11:
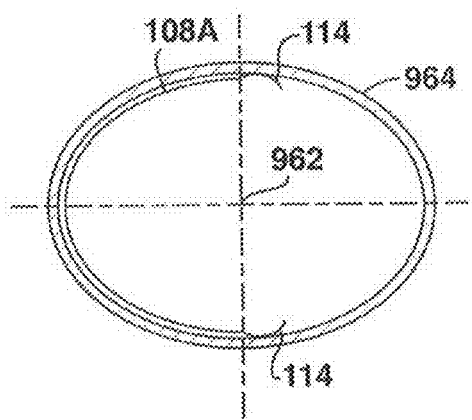

FIG. 9 illustrates first stent 102A delivered to the target location at bifurcated vessel 960. Access to the vasculature may be achieved, for example, through a branch of the femoral artery. In general, a guidewire (not shown) is introduced into the target vessel and a first stent delivery system is then tracked over the guidewire and threaded through the vascular system of the patient until O-shaped body 110A of first stent 102A extends within first branch vessel 966 and C-shaped body 108A of first stent 102A extends within-main vessel 964. FIG. 9 illustrates first stent 102A in the compressed or delivery configuration. As shown, C-shaped body section 108A of first stent 102A is oriented within main vessel 964 such that the open portion 120A (see FIGS. 4, 5) of C-shaped body section 108A faces toward a longitudinal axis 962 of main vessel 964. Once the first stent delivery system is in place as desired, the sheath constraining first stent 102A is retracted to allow first stent 102A to self-expand. Upon expansion, O-shaped body 110A of first stent 102A is deployed against the inner wall of first branch vessel 966 and C-shaped body 108A of first stent 102A expands within main vessel 964. If necessary, first stent 102A may be further expanded by inflating a balloon of the first stent delivery system or by a balloon of a separate, independent balloon catheter. The first stent delivery and/or the separate, independent balloon catheter are then removed from the patient, leaving first stent 102A in place within bifurcated vessel 960. FIG. 10 shows first stent 102A in its expanded or deployed configuration. FIG. 11 is a schematic cross-sectional view taken along line 11-11 of FIG. 10. As can be seen in FIG. 11, C-shaped body section 108A of first stent 102A covers approximately half of main vessel 964, and sockets 114 face each other generally across longitudinal axis 962 of main vessel 964.

Figure 12:
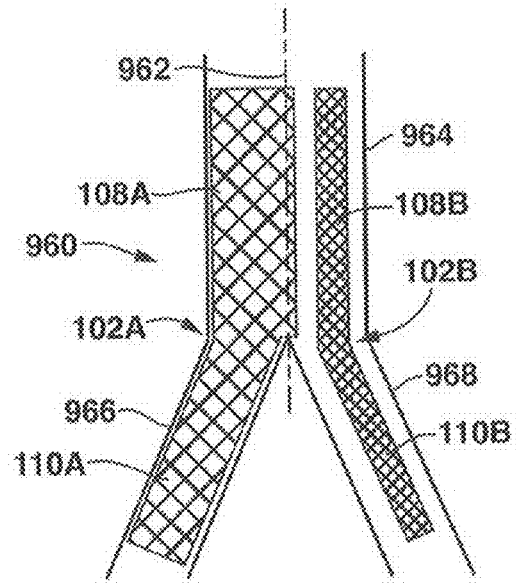

As shown in FIG. 12, second stent 102B is delivered via a second stent delivery system such that second stent 102B is positioned beside or adjacent to first stent 102A. The second stent delivery system may be any delivery system described herein. O-shaped body 110B of second stent 102B extends within second branch vessel 968 and C-shaped body 108B of second stent 102B extends within main vessel 964. As shown, C-shaped body section 108B is oriented within main vessel 964 such that the open portion 120B of the C-shaped body section 108B faces toward longitudinal axis 962 of rain vessel 964. FIG. 12 illustrates second stent 102A in the compressed or delivery configuration. Once the second stent delivery system is in place as desired, the sheath constraining second stent 102B is withdrawn to allow second stent 102B to self-expand. Upon expansion, O-shaped body 110B of second stent 102B is deployed against the inner wall of second branch vessel 968 to maintain the opening and C-shaped body 108B of second stent 102B expands %4ithin main vessel 964.

Figure 13:
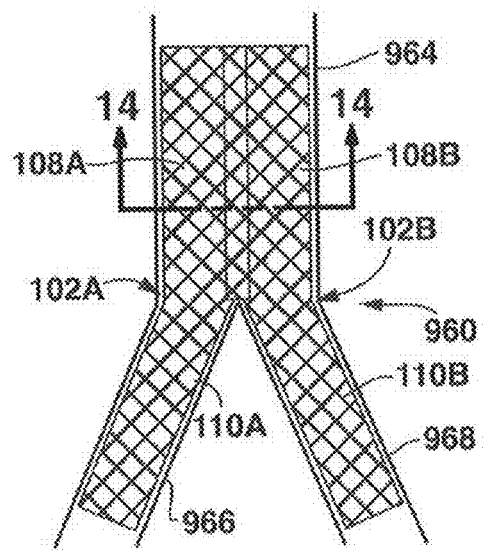
Figure 14:
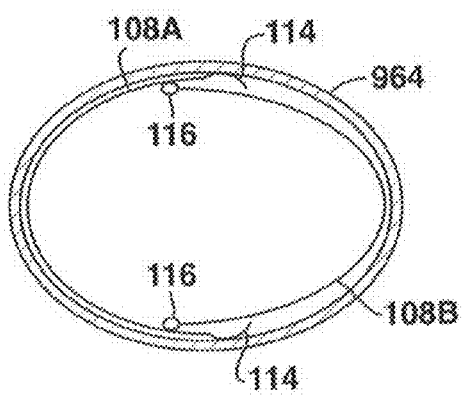
Figure 15:
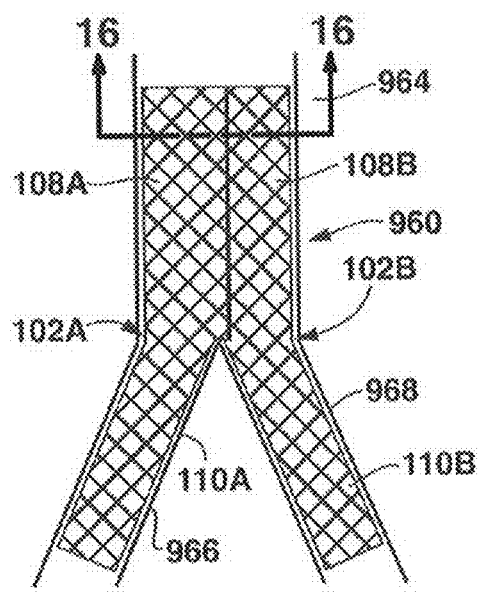
Figure 16:
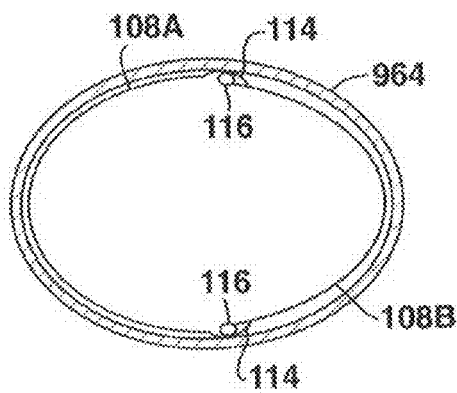

At this point in the delivery process, as shown in FIGS. 13 and 14, the two C-shaped body sections (108A, 108B) are aligned side by side within main vessel 964. Edges 118A and 118B of C-shaped body sections 108A, 108B overlap as shown in FIG. 14. Further, sockets 114 of first stent 102A are correspondingly aligned with tabs 116 of second stent 102B. A balloon catheter or pair of side-by-side balloon catheters may be inserted to further expand C-shaped body section 108B or both C-shaped body sections 108A, 08B such that tabs 116 slide into sockets 114, as shown in FIG. 16. Balloon expansion may not be necessary in the case where self-expansion of C-shaped body section 108B is sufficient to cause tabs 116 to slide into sockets 114. In such a situation, FIGS. 13 and 14 show C-shaped body section 108B during self-expansion and FIGS. 15 and 16 show C-shaped body section 108B at the completion of self-expansion. With tabs 116 engaged with-receptacles 114, C-shaped body section 108A is maintained in an edge-to-edge abutting relationship with C-shaped body section 108B so that a tubular or cylindrical stent prosthesis is formed in vivo within main vessel 964. Finally, a balloon of the second stent delivery system or a balloon of a separate, independent balloon catheter may be inflated to further expand the joined C-shaped body sections 108A, 108B together to a desired diameter if self-expansion does not achieve the desired diameter. Alternatively, side-by-side balloon catheters may be used to further expand the joined C-shaped body-sections 108A, 108B in the so-called "kissing balloons" technique.

The second stent delivery and/or the separate, independent balloon catheter are then removed from the patient, leaving deployed stents 102A, 102B implanted within bifurcated vessel 960.

As shown in FIGS. 9-16, second stent 102B is implanted and deployed independently from first stent 102A. Accordingly, a clinician may custom select an appropriate stent size for second stent 102B if second branch vessel 968 is of a different lumen diameter than first branch vessel 966. Such differential sizing of second stent 102B may occur even after first stent 102A is implanted.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent system for placement in a bifurcated body vessel, the stent system comprising:
   first and second self-expanding stent prostheses, each prosthesis being adapted to be radially contracted within a sheath to a compressed configuration for delivery into the body vessel and having a mechanical shape memory of an expanded configuration, each prosthesis comprising:
   a generally hem icylindrical section defined by a pair of opposing spaced apart edges extending along a length thereof and a body extending between the edges to form a generally C-shaped cross-section along the length of the hemicylindrical section; and
   a first generally cylindrical section axially coupled to the generally hemicylindrical section of the first stent prosthesis and a second generally cylindrical section axially coupled to the generally hemicylindrical section of the second stent prosthesis, the first and second generally cylindrical sections form respective legs of the bifurcated scaffold, wherein, the first and second self-expanding stent prostheses assume the expanded configuration when released from the sheath such that the edges of the generally hemicylindrical section of the first prosthesis mate and form a single interlock extending substantially along the length of the edges thereof with the corresponding edges of the generally hemicylindrical section of the second prosthesis to form a tubular trunk portion of a bifurcated scaffold when assuming the expanded configuration within a vessel.

2. The stent system of claim 1, wherein the first generally hemicylindrical section includes a first edge and a second edge and at least a first socket disposed on the first edge and a second socket disposed on the second edge, wherein the second generally hemicylindrical section includes a third edge and a fourth edge and at least a first tab disposed on the third edge and a second tab disposed on the fourth edge, and wherein the first and second tabs are configured to be received in the first and second sockets, respectively.

3. The stent system of clam 2, wherein the first generally hemicylindrical section includes a plurality of sockets on the first edge and a plurality of sockets on the second edge, wherein the second generally hemicylindrical section includes a plurality of tabs on the third edge and plurality of tabs on the fourth edge, and wherein the tabs are configured to be received in respective sockets.

4. The stent system of claim 2, wherein the sockets and the tabs are formed of a radiopaque material.

5. The stent system of claim 1, wherein the first generally hemicylindrical section includes a first edge and a second edge and at least a first female component disposed on the first edge and a second female component disposed on the second edge, wherein the second generally hemicylindrical section includes a third edge and a fourth edge and at least a first male component disposed on the third edge and a second male component disposed on the fourth edge, and wherein the first and second male components are configured to be received in the first and second female components, respectively.

6. The stent system of claim 5, wherein at least one of the first and second female components comprises an elongate groove extending the entire length of the first or second edge, respectively.

7. The stent system of claim 1, wherein the first generally cylindrical section is coupled to the generally hemicylindrical section of the first stent prosthesis by a junction, wherein the junction comprises frame members from the first generally cylindrical section continuous with the frame members from the generally hemicylindrical section of the first stent prosthesis.

8. The stent system of claim 1, wherein the second generally cylindrical section is coupled to the generally hemicylindrical section of the second stent prosthesis by a junction, wherein the junction comprises frame members from the second generally cylindrical section continuous with the frame members from the generally hem icylindrical section of the second stent prosthesis.

9. A method of implanting a stent system in a bifurcation having a main vessel, a first branch vessel, and a second branch vessel, the method including the steps of:

releasing a first self-expanding stent prosthesis from a compressed configuration within a sheath to an expanded configuration at the bifurcation such that a first generally hemicylindrical section thereof expands into contact with a wall of the main vessel of the bifurcation and a first generally cylindrical section thereof expands into contact with a wall of the first branch vessel of the bifurcation, the first generally hemicylindrical section defined by a pair of opposing spaced apart edges extending along a length thereof, the first generally hemicylindrical section being axially coupled to the first hemicylindrical section the first hemicylindrical section having a generally C-shaped cross-section along its length when the first stent is in the expanded configuration; and releasing a second self-expanding stent prosthesis from a compressed configuration within a sheath to an expanded configuration at the bifurcation such that a second generally hemicylindrical section thereof expands into contact with a wall of the main vessel of the bifurcation and a second generally cylindrical section thereof expands into contact with a wall of the second branch vessel of the bifurcation, the second generally hemicylindrical section defined by a pair of opposing spaced apart edges extending along a length thereof, the second generally hemicylindrical section being axially coupled to the second hemicylindrical section the second hemicylindrical section having a generally C-shaped cross-section along its length when the first stent is in the expanded configuration;

wherein the second generally hemicylindrical section and the first generally hemicylindrical section mate and form a single interlock extending substantially along the length of the corresponding edges to form a tubular trunk portion of a bifurcated scaffold while the generally cylindrical sections of the first and second stent prostheses form respective legs of the bifurcated scaffold.

10. The method of claim 9, wherein the step of releasing the second stent prosthesis further includes inflating a balloon to further expand the second generally hemicylindrical section into the abutting relationship with the first generally hemicylindrical section.

11. The method of claim 9, wherein the first generally hemicylindrical section includes a first edge and a second edge and at least a first socket disposed on the first edge and a second socket disposed on the second edge, wherein the second generally hemicylindrical section includes a third edge and a fourth edge and at least a first tab disposed on the third edge and a second tab disposed on the fourth edge, and wherein the step of deploying the second stent prosthesis includes aligning the first and second tabs such that the first and second tabs are received in the first and second sockets, respectively.

* * * * *